(12) United States Patent
Hoenes et al.

(10) Patent No.: US 9,063,102 B2
(45) Date of Patent: Jun. 23, 2015

(54) CONSUMABLE ELEMENT MAGAZINE FOR A MEASURING SYSTEM FOR DETERMINING AN ANALYTE CONCENTRATION

(75) Inventors: Joachim Hoenes, Zwingenberg (DE); Uwe Kraemer, Ilvesheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 0 days.

(21) Appl. No.: 13/218,215

(22) Filed: Aug. 25, 2011

(65) Prior Publication Data
US 2012/0051983 A1 Mar. 1, 2012

Related U.S. Application Data

(63) Continuation of application No. PCT/EP2010/000563, filed on Jan. 30, 2010.

(30) Foreign Application Priority Data

Feb. 26, 2009 (EP) .................................. 09002722

(51) Int. Cl.
*B01L 3/00* (2006.01)
*G01N 31/22* (2006.01)
(Continued)

(52) U.S. Cl.
CPC .............. *G01N 35/00732* (2013.01); *G01N 2035/00089* (2013.01); *A61B 5/1411* (2013.01); *A61B 5/14532* (2013.01); *A61B 5/15146* (2013.01); *A61B 5/157* (2013.01); *A61B 2562/0295* (2013.01); *B01L 99/00* (2013.01); *B01L 2300/022* (2013.01); *B01L 2300/024* (2013.01); *B01L 2300/0825* (2013.01); *G01N 33/4875* (2013.01); *G01N 35/00663* (2013.01);
(Continued)

(58) Field of Classification Search
CPC ................... A61B 5/14532; B01L 2300/0825; G01N 2035/00089; G01N 31/22; G01N 33/54386; G01N 33/4875; G01N 33/48757
USPC ...................... 221/1; 422/430, 554
See application file for complete search history.

(56) References Cited

U.S. PATENT DOCUMENTS 6,497,845 B1 12/2002 Sacherer
2003/0211012 A1 11/2003 Bergstrom et al.
(Continued)

FOREIGN PATENT DOCUMENTS

| EP | 1950562 A2 | 7/2008 |
|---|---|---|
| WO | WO 03082091 A2 * | 10/2003 |
| WO | 2005098431 A1 | 10/2005 |
| WO | 2008127892 A2 | 10/2008 |

*Primary Examiner* — Dennis M White
*Assistant Examiner* — Bryan Kilpatrick
(74) *Attorney, Agent, or Firm* — Harness Dickey

(57) ABSTRACT

The invention relates to a magazine for a device of a measuring system for determining an analyte concentration in a body fluid sample, wherein the magazine contains consumable analytical elements in a plurality of chambers. According to the invention, a data carrier, on which information is stored, is fastened to the magazine, the information indicating which magazine chambers are not intended for removal of a consumable element due to manufacturing defects. The invention further relates to a device, the control unit of which suppresses access by the removal unit to predefined magazine chambers, to a measuring system comprising such a device and a magazine, and to a method for controlling the removal unit of the device.

15 Claims, 1 Drawing Sheet

(51) Int. Cl.
*G01N 33/52* (2006.01)
*A61B 5/15* (2006.01)
*A61B 5/151* (2006.01)
*A61B 5/157* (2006.01)
*B01L 99/00* (2010.01)
*G01N 33/487* (2006.01)
*G01N 35/00* (2006.01)
*G07F 11/00* (2006.01)
*A61B 5/145* (2006.01)

(52) U.S. Cl.
CPC ........... *G01N2035/00801* (2013.01); *G01N 2035/00851* (2013.01)

(56) References Cited

U.S. PATENT DOCUMENTS

| | | |
|---|---|---|
| 2004/0260325 A1 | 12/2004 | Kuhr et al. |
| 2005/0009122 A1 | 1/2005 | Whelan et al. |
| 2006/0189895 A1 | 8/2006 | Neel et al. |
| 2007/0009381 A1 | 1/2007 | Schulat et al. |
| 2007/0293790 A1 | 12/2007 | Bainczyk et al. |
| 2007/0299458 A1 | 12/2007 | Epple |
| 2008/0034834 A1* | 2/2008 | Schell .............. 73/1.02 |
| 2008/0034835 A1* | 2/2008 | Schell .............. 73/1.02 |
| 2009/0022630 A1 | 1/2009 | Hoenes et al. |

* cited by examiner

CONSUMABLE ELEMENT MAGAZINE FOR A MEASURING SYSTEM FOR DETERMINING AN ANALYTE CONCENTRATION

CROSS-REFERENCE TO RELATED APPLICATIONS

This application is a continuation of International Application No. PCT/EP2010/000563, filed on Jan. 30, 2010, which claims the benefit and priority of European Patent Application No. 09002722.8, filed on Feb. 26, 2009. The entire disclosures of the above applications are incorporated herein by reference.

BACKGROUND

The invention relates to a magazine for a device of a measuring system for determining an analyte concentration in a body fluid sample. Such a system, which contains consumable analytical elements, for example lancets or test elements, in a plurality of chambers, is described in EP 0 951 939 B1 (see also, U.S. Pat. No. 6,497,845 B1). The invention further relates to a measuring system comprising such a magazine and to a method for controlling a removal unit of such a device, with which consumable elements can be removed from the chambers of an inserted magazine.

Magazines of consumable elements for measuring systems for determining analyte concentrations in human or animal body fluid samples must adhere to strict manufacturing tolerances for the chambers of a magazine to be filled automatically with consumable elements and for these elements to be removed without damage by a removal unit of a handheld device. Even small deviations from a defined chamber geometry can cause the consumable element to jam in a magazine chamber and therefore not be removed, or the respective magazine chamber cannot be filled with a consumable element at all.

Typically, these magazines are discarded after the consumable elements contained therein have been used. The costs associated with the production of magazines therefore account for a considerable portion of the overall costs of a measuring system or a measurement for determining an analyte concentration of a body fluid sample. This applies in particular to magazines comprising a relatively large number of chambers for small consumable elements because the manufacturing tolerances that must be adhered to become stricter as the miniaturization increases. On the other hand, however, the costs of a magazine must be apportioned among the number of consumable elements contained therein, and hence among the number of measurements that are possible with the magazine, which tends to lead to rising overall costs for a reduced number of magazine chambers.

SUMMARY

It is therefore an object of the present invention to show a way of how the costs per measurement can be lowered for a measuring system for determining an analyte concentration of a body fluid sample.

In various embodiments, the present invention provides a magazine for a device of a measuring system for determining an analyte concentration in a body fluid sample, the magazine containing consumable analytical elements in a plurality of chambers, characterized in that a data carrier, on which information is stored, is fastened to the magazine, the information indicating which magazine chambers are not intended for removal of a consumable element due to manufacturing defects. Also provided is a measuring system for determining an analyte concentration of a body fluid sample, comprising a magazine and a device in which the magazine can be inserted and which comprises a removal unit for removing the consumable elements from the magazine chambers, characterized in that the device comprises a reader for reading the data carrier fastened to the magazine and a control unit connected to the reader, the control unit suppressing access by the removal unit to chambers that, according to the information stored on the data carrier, are not intended for removal of a consumable element due to manufacturing defects.

In various embodiments, the present invention provides a device, comprising a compartment for inserting a magazine, which contains consumable analytical elements in a plurality of chambers, and a removal unit for removing the consumable elements from the magazine chambers, characterized in that the device comprises a control unit which suppresses access by the removal unit to predefined chambers. Also provided is a method for controlling a removal unit of a device of a measuring system, the unit being used to remove consumable analytical elements from chambers of a magazine that is inserted in the device, the magazine being moved incrementally in the device so that the magazine chambers consecutively arrive in a removal position in which the removal unit can access the respective chamber and remove a consumable element, wherein a data carrier is read, which is fastened to a magazine containing consumable analytical elements in magazine chambers, information stored on the data carrier is evaluated, the information indicating which magazine chambers are not intended for removal of a consumable element due to manufacturing defects, and the magazine is advanced by one increment and the next chamber is brought into the removal position before the removal unit gains access, as soon as a magazine chamber that is not intended for removal of a consumable element due to manufacturing defects is in the removal position.

Instead of looking at the costs of a measurement associated with the magazine by entering into an optimal compromise between the increasing production costs of a magazine with a rising number of chambers and the decreasing basis among which the production costs of a magazine can be apportioned as the number of chambers declines, the present invention pursues a different avenue and deliberately accepts production defects for individual magazine chambers.

Because it is not imperative with the magazine according to the invention to adhere to manufacturing tolerances for all chambers, but instead the fact that individual chambers are unfit for use is accepted, a considerable portion of the production costs can be saved. The expenditure for producing all chambers in a magazine that comprises, for example, 20 or more chambers without defects is considerably higher than for a correspondingly sized magazine for which it is accepted that some chambers are not usable due to manufacturing defects.

By reading a data carrier fastened to the magazine, the control module of a device can determine which chambers in a magazine according to the invention are not intended for removal of a consumable element due to manufacturing defects. Although several chambers in the magazine according to the invention may not be functional, the magazine can still be used without impairing the user comfort.

The magazine chambers not intended for the removal of consumable elements due to manufacturing defects can be empty, but do not have to be. Particularly simple manufacturing can be achieved in many cases by equipping all magazine chambers with consumable elements. While it is not possible to remove the consumable elements from defective chambers without damage, or perhaps not at all, filling can be particularly efficient if all chambers are filled, which is generally possible when damage to the consumable elements is accepted with substantially forceful insertion.

Each magazine chamber preferably contains no more than a single consumable element. In principle, however, it is possible to store two consumable elements, for example a lancet and a separate test strip, in a chamber.

The magazine chambers preferably each have two, notably opposing, openings. In this way, consumable elements can be removed particularly efficiently by pushing a removal element into an opening and thereby pushing the consumable element out of another opening. In principle, however, a single opening per magazine chamber is sufficient with an appropriate design of the removal unit.

The data carrier fastened to a magazine according to the invention can be a bar code, for example. The data carrier, however, is preferably an electronic memory, for example flash EEPROM (electrically erasable programmable read-only memory) or an RFID (radio-frequency identification) chip.

The consumable elements contained in a magazine according to the invention can be, for example, lancets, test elements, or lancets with integrated test elements. A magazine according to the invention preferably has at least 20 chambers, with at least 40 being particularly preferred, and more particularly at least 50. In a magazine according to the invention, preferably at least one chamber is not intended for removal of a consumable element due to a manufacturing defect, for example two to four chambers. In the magazine according to the invention, it is particularly preferred if up to 10% of the chambers are not intended for removal of a consumable element.

According to an advantageous refinement of the invention, the magazine chambers that are not intended for removal of a consumable element due to manufacturing defects are closed by a film just like the magazine chambers that are intended for removal of a consumable element. In this way, production can be particularly efficient. The magazine chambers sealed with a foil, which due to manufacturing defects are not intended for removal of a consumable element, can contain consumable elements or be empty. Preferably all magazine chambers are closed by a film.

However, notably with rotational magazines, for example disk or revolver magazines, which are rotated incrementally in the device, it may be advantageous to not close a chamber with a film and not fill it. With such a chamber, unambiguous numbering of the chambers can be easily achieved by making the empty, open chamber the first chamber and continuously counting the remaining chamber from there clockwise or counterclockwise. The data carrier of a magazine can store, for example, the numbers of the chambers not intended for removal of a consumable element due to manufacturing errors. It is also possible, as an alternative or in addition, to store the numbers of the functional chambers on the data carrier.

In addition to a magazine, a measuring system according to the invention for determining an analyte concentration of a body fluid sample also includes a device in which the magazine can be inserted and which comprises a removal unit for removing the consumable elements from the magazine chambers. A device according to the invention is preferably a handheld device and has a compartment for introducing a magazine, the compartment containing expendable analytical elements in a plurality of chambers, and a removal unit for removing the consumable elements from chambers of an introduced magazine as well as a control unit, which suppresses access to predefined chambers by the removal unit.

Preferably access is suppressed to chambers which are not intended for removal of consumable elements due to manufacturing defects. However, it is possible for the control unit to allow only a predefined maximum number of measurements per magazine and prevent the removal of excess consumable elements. To this end, it is possible to always suppress the removal of excess consumable elements, or to make it dependent on the fulfillment of predefined conditions. For example, excess consumable elements can be used to compensate for operating errors, so that a user can perform the number of measurements intended for a magazine despite a failed sample withdrawal or measuring attempt. It is also possible to clear initially blocked chambers so as to reward a user, for example for performing measurements on a regular basis.

The device of a measuring system according to the invention preferably has a read device for reading the data carrier fastened to the magazine and a control unit connected to the read device, the control unit suppressing access by the removal unit to chambers that according to the information stored on the data carrier are not intended for removal of a consumable element due to manufacturing defects. Advantageously, it can be achieved by the control unit of a device according to the invention that a user does not even notice when no consumable element can be removed from individual chambers with an inserted magazine. The information stored on the data carrier of the magazine makes it possible for the removal unit to access only those magazine chambers from which in fact a functional consumable element can be removed. Chambers unfit for use can simply be skipped.

In the simplest case, consumable elements are removed from a magazine in a measuring system according to the invention until removal of functional consumable elements is no longer possible and the magazine is subsequently disposed of. A magazine comprising, for example, 54 chambers, which can be sold by a manufacturer with the guarantee that at least 50 functional consumable elements can be removed from the magazine, thus offers the possibility that up to four chambers are not intended for removal of the consumable element due to functional defects. In such a case, the magazines brought to market would thus contain 50 to 54 functional consumable elements. Users could then hope that more than the guaranteed minimum number of consumable elements can be removed from the acquired magazine. However, such hopes would be spoiled more or less frequently because some magazines will indeed contain only the guaranteed number of consumable elements.

It may therefore be advantageous for the control unit to suppress access by the removal unit to chambers of a magazine as soon as a predefined maximum number of consumable elements, for example the guaranteed minimum number, have been removed from the magazine. In this way, it can be achieved that always only the guaranteed number of consumable elements can be removed from a magazine. In this way, disappointment by the user, which could lead to dissatisfaction, can be avoided.

Overfilling occurring frequently with the magazines of a measuring system according to the invention, which is to say the fact that the number of functional consumable elements contained in a magazine is generally greater than a guaranteed minimum number, however, can also be used to provide users in special cases with a larger number of consumable elements, for example when it was not possible to perform a measurement with a consumable element or an obviously erroneous measured value was generated.

If the lancing depth, for example, is not adjusted deep enough for a handheld device, it is possible that a lancet prick does not supply a body fluid sample, or one that is not sufficiently large. In some exceptions it is also possible for cold fingers, for example, to cause a lancet prick to fail to obtain body fluid, or a sufficient amount of body fluid. In these and similar cases, the control unit of a measuring system according to the invention can allow additional access by the removal unit to functional chambers of the magazine, which is to say increase, for example by 1, the maximum number of consumable elements removed after which access by the removal unit to chambers of the magazine is suppressed. If the magazine in such a case contains more than the guaranteed minimum number of consumable elements, in this way an operating error by a user can be compensated for, so that the user can perform the intended number of body fluid analyses with the magazine.

In such an embodiment, the predefined maximum number for an inserted magazine is a variable, which after the insertion of a new magazine is reset to a default value, for example the guaranteed minimum number of functional consumable elements contained in a magazine.

The removal unit of a device according to the invention can be controlled in particular by a method having the features described in claim 15.

DRAWINGS

Further details and advantages of the invention will be described hereinafter.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
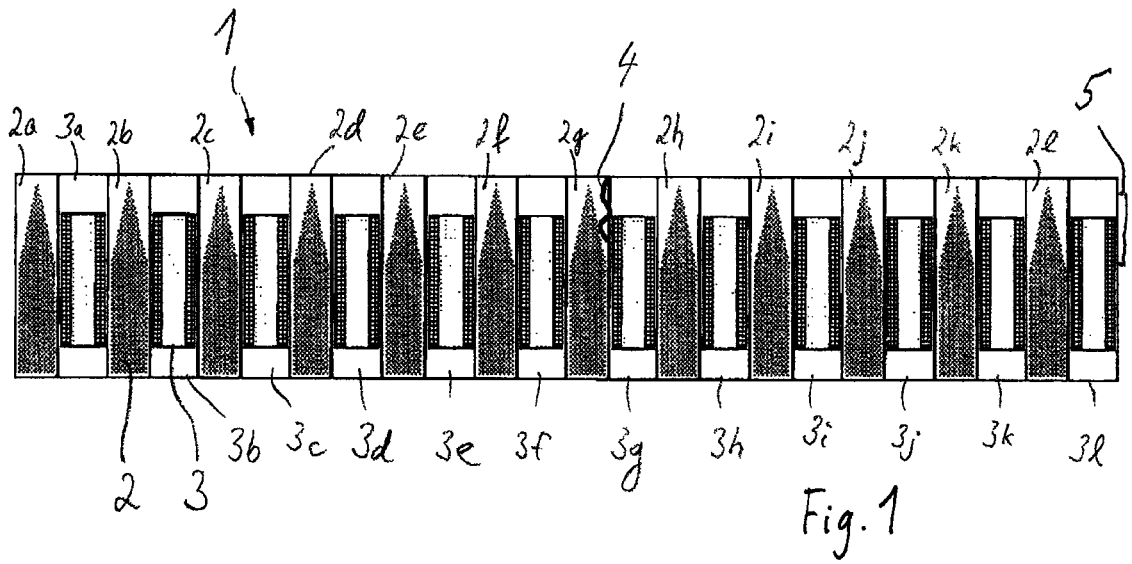
FIG. 1 is a schematic illustration of an exemplary embodiment of a magazine according to the invention.
Figure 2:
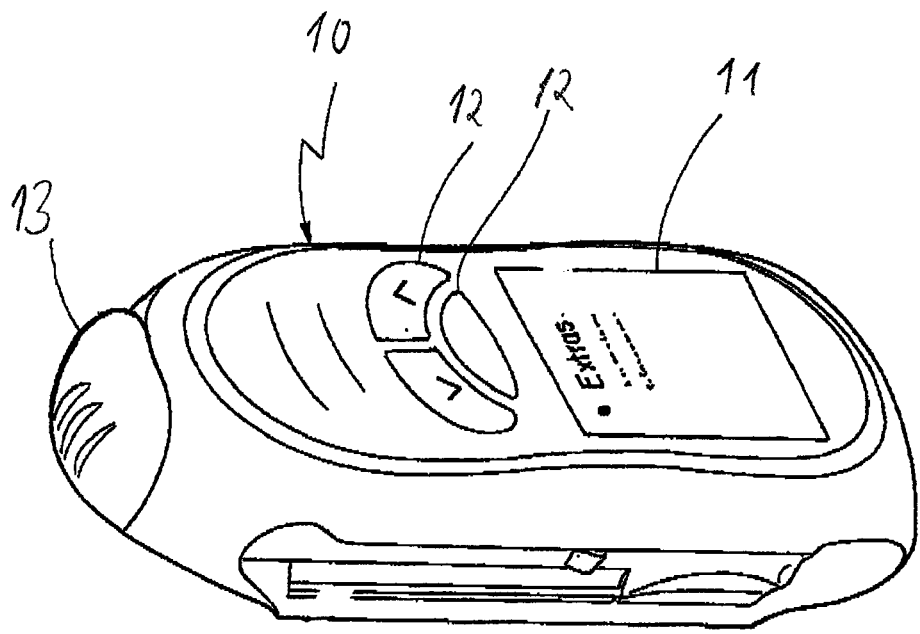
FIG. 2 is a schematic illustration of a handheld device in which the magazine can be inserted.

FIG. 1 is a schematic illustration of a magazine 1 for a handheld device 10 of a measuring system for determining an analyte concentration in a body fluid sample, the device being shown in FIG. 2. The magazine 1 contains lancets 2 and test elements 3 as consumable elements, which are each arranged individually in separate chambers 2*a*-2*l*, 3*a*-3*l* of the magazine 1. Each of the magazine chambers 2*a*-2*l*, 3*a*-3*l* has two opposing openings, which are each closed by a film. By sliding in a ram of a removal unit of a handheld device 10, the consumable elements 2, 3 can be removed from the magazine chambers 2*a*-2*l*, 3*a*-3*l*.

The magazine 1 is an injection-molded part made of synthetic material. Wear of the injection mold or faulty injection molding parameters can lead to manufacturing defects, so that one or more chambers of such a magazine do not meet the predefined manufacturing tolerances and therefore are unfit for use.

In the shown exemplary embodiment, one of the magazine chambers, more specifically the chamber 2*g*, has a manufacturing defect 4, so that the consumable element 2 arranged in this chamber cannot be removed, or only with great difficulty.

A data carrier 5 is fastened to the magazine 1. The data carrier 5 stores information indicating which of the magazine chambers 2*a*-2*l*, 3*a*-3*l* are not intended for removal of a consumable element 2, 3 due to manufacturing defects. The data carrier 5 can be, for example, a bar code or a magnetic memory. The data carrier 5, however, is preferably an electronic memory, notably an RFID chip. The information stored on the data carrier can indicate, for example, for each individual chamber 2*a*-2*l*, 3*a*-3*l* whether or not this chamber is intended for removal of a consumable element 2, 3. However, in principle it suffices, for example, to indicate in a list the chambers that are not intended for removal of a consumable element 2, 3 due to manufacturing defects, or to indicate only the chambers that fulfill predefined manufacturing tolerances.

FIG. 2 shows a schematic illustration of a handheld device 10, in which the magazine 1 shown in FIG. 1 can be inserted. Such a handheld device 10 can be, for example, a lancing device or a measuring device for determining an analyte concentration of a body fluid sample, for example the glucose or lactate concentration. The shown handheld device 10 is a measuring device for determining the glucose concentration and a lancing device at the same time.

The handheld device 10 has a display unit 11, for example a liquid crystal display, and operating elements in the form of buttons 12. A protective cap 13 of the device 10 closes a housing opening, against which a body part can be placed for obtaining a blood sample. The handheld device 10 is supplied with power by means of batteries, which can be inserted in a battery receiving compartment of the device.

On the back, the handheld device 10 has a compartment, which is not shown, for a magazine 1 comprising consumable elements 2, 3. When a magazine 1 is inserted, the data carrier 5 fastened to the magazine 1 is read by a reader of the handheld device 10, and the information stored on the data carrier 5 with regard to which magazine chambers are not intended for removal of a consumable element 2, 3 due to manufacturing defects is forwarded to a control unit, which is not shown, for example a microprocessor, and evaluated by the same.

The handheld device 10 has a removal unit, which is not shown, for removing the consumable elements 2, 3 from the magazine chambers 2*a*-2*l*, 3*a*-3*l*. This removal unit can be designed, for example, as a ram, which penetrates a magazine opening for the removal and pushes a consumable element 2, 3 out of a chamber opening arranged on the opposite side. The control unit suppresses access by the removal unit to chambers that, according to the information stored on the data carrier 5, are not intended for removal of a consumable element 2, 3 due to manufacturing defects, for example by advancing the magazine 1 by one increment as soon as a magazine chamber 2*g* that is not intended for removal of a consumable element due to manufacturing defects is in the removal position and by bringing the next chamber 2*h* in a usage position before the removal unit gains access.

The control unit of the shown handheld device 10 suppresses access by the removal unit to closed chambers 2*a*-2*l*, 3*a*-3*l* of the magazine 1 as soon as a predefined maximum number of consumable elements 2, 3 have been removed from the magazine 1. This maximum number can correspond, for example, to a guaranteed minimum number of functional consumable elements 2, 3 of a magazine. For example, with the magazine 1 shown in FIG. 1, the manufacturer could guarantee that ten functional lancets 2 can be removed. In principle, however, eleven lancets 2 could be removed from the magazine 1 shown in FIG. 1 because only a single magazine chamber 2g is defective.

The control unit can suppress the removal of an eleventh lancet, so that always the same number of lancets 2, more specifically only the guaranteed minimum number, can be removed from all magazines 1 of the measuring system that are sold. The predefined maximum number can be stored in an electronic memory of the handheld device 10. This is an example of a case in which the predefined maximum number is independent of the number of chambers that are not intended for removal of the consumable element due to manufacturing defects, which is to say corresponds, for example, to the minimum number of functional consumable elements guaranteed by the manufacturer. However, it is also possible for the predefined maximum number for an inserted magazine 1 to be a variable, which is reset to a default value after a new magazine 1 is inserted. For example, the control unit can increase the maximum number by one if, after removal of a consumable element 2, 3, no measurement is carried out within a predefined period of time, or the measurement result is outside of a predefined range. In this way, excess consumable elements 2, 3 can be used for failed measuring attempts so as to enable a user to perform the intended number of measurements per magazine 1.

REFERENCE NUMERALS

1 Magazine
2 Lancets
2a-2l Magazine chambers
2g Defective magazine chamber
3a-3l Magazine chambers
4 Manufacturing defect
5 Data carrier
10 Handheld device
11 Display unit
12 Buttons
13 Protective cap

What is claimed is:

1. A magazine for a device of a measuring system for determining an analyte concentration in a body fluid sample, the magazine containing consumable analytical elements in a plurality of chambers, wherein the consumable analytical elements are lancets and/or test elements and wherein one or more of the plurality of chambers has a manufacturing defect, wherein a data carrier is fastened to the magazine, the data carrier storing manufacturing defect information therein and providing the stored manufacturing defect information to a control unit indicating which magazine chambers are not intended for removal of one of the consumable analytical elements due to the manufacturing defect of the chamber.

2. The magazine according to claim 1, wherein the data carrier comprises electronic memory.

3. The magazine according to claim 1, wherein the data carrier comprises an RFID chip.

4. The magazine according to claim 1, wherein the magazine chambers that are not intended for removal of a consumable analytical element due to manufacturing defects are closed by a film as are the magazine chambers that are intended for removal of a consumable analytical element.

5. The magazine according to claim 1, wherein each of the magazine chambers contains no more than one consumable analytical element.

6. A measuring system for determining an analyte concentration of a body fluid sample, comprising a magazine and a device in which the magazine can be inserted and which comprises a removal unit for removing consumable analytical elements from magazine chambers, wherein (1) the magazine contains consumable analytical elements in a plurality of chambers, wherein the consumable analytical elements are lancets and/or test elements wherein a data carrier is fastened to the magazine, the data carrier stores and provides information indicating which magazine chambers are not intended for removal of one of the consumable analytical elements due to manufacturing defects of the chambers; and (2) the device comprises a reader for reading the data carrier fastened to the magazine and the device further comprises a control unit connected to the reader, the control unit configured to suppress access by the removal unit to chambers that, according to the information stored on the data carrier, are not intended for removal of one of the consumable analytical elements due to manufacturing defects of the chambers.

7. The measuring system according to claim 6, wherein the control unit suppresses access by the removal unit to chambers of the magazine as soon as a predefined maximum number of consumable analytical elements have been removed from the magazine.

8. The measuring system according to claim 7, wherein the predefined maximum number is independent of the number of chambers that are not intended for removal of one of the consumable analytical elements due to manufacturing defects.

9. The measuring, system according to claim 7, wherein the predefined maximum number is stored in an electronic memory of the device.

10. The measuring system according to claim 9, wherein the predefined maximum number for an inserted magazine is a variable, which is reset to a default value after a new magazine is inserted.

11. The measuring system according to claim 10, wherein the control unit increases the maximum number by one if, after removal of one of the consumable analytical elements, no measurement is carried out within a predefined period of time, or the measurement result is outside of a predefined range.

12. The measuring system according to claim 7, wherein the predefined maximum number is a constant that is identical for all magazines of the system.

13. A method for controlling a removal unit of a device of a measuring system, the unit being used to remove consumable analytical elements from chambers of the magazine of claim 1 that is inserted in the device, the magazine being moved incrementally in the device so that the magazine chambers consecutively arrive in a removal position in which the removal unit can access the respective chamber and remove an consumable element, wherein a data carrier is read, which is fastened to a magazine containing consumable analytical elements in magazine chambers,
information stored on the data carrier is evaluated, the information indicating which magazine chambers are not intended for removal of an consumable element due to manufacturing defects, and
the magazine is advanced by one increment and the next chamber is brought into the removal position before the removal unit gains access, as soon as a magazine chamber that is not intended for removal of an consumable element due to manufacturing defects is in the removal position.

14. A measuring system for determining an analyte concentration of a body fluid sample, comprising the magazine of claim 1 containing consumable analytical elements in a plurality of chambers and
a device in which the magazine can be inserted and which comprises a removal unit for removing the consumable elements from the magazine chambers and a control unit,
wherein the control unit suppresses access by the removal unit to chambers of a magazine as soon as a predefined maximum number of consumable elements has been removed from the magazine, said predefined maximum number being a variable, which is reset to a default value after a new magazine is inserted.

15. A measuring system for determining an analyte concentration of a body fluid sample, the measuring system comprising:
- a magazine defining a plurality of chambers containing consumable analytical elements including lancets and/or test elements, wherein one or more of the plurality of chambers comprises a manufacturing defect;
- a data carrier fastened to the magazine, the data carrier including electronic memory configured to store and provide information indicating the one or more chambers having the manufacturing defect;
- a device for receiving insertion of the magazine, the device comprising:
  - a removal unit for removing the consumable analytical elements from the plurality of chambers;
  - a reader for reading the data carrier; and
  - a control unit connected to the reader, the control unit configured to suppress access by the removal unit to chambers that, according to the information stored on the data carrier, have a manufacturing defect and are not intended for removal of one of the consumable analytical elements.

* * * * *